Feb. 7, 1961 E. B. PARKER Plant Pat. 2,019
CHRYSANTHEMUM PLANT
Filed March 7, 1960
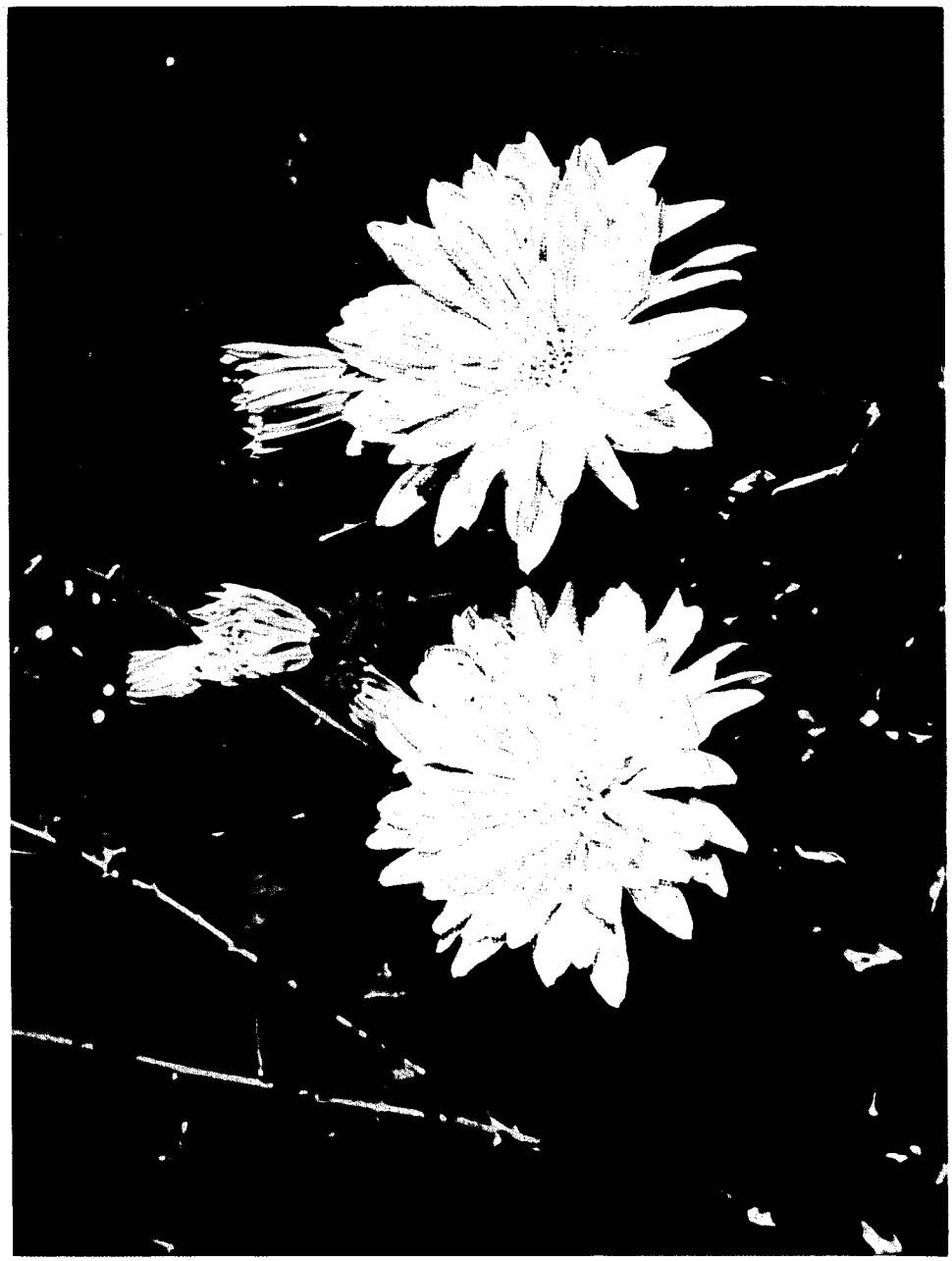
INVENTOR
ELIZABETH B. PARKER
BY John Joseph Hale
ATTORNEY.

United States Patent Office

Plant Pat. 2,019
Patented Feb. 7, 1961

2,019

CHRYSANTHEMUM PLANT

Elizabeth B. Parker, 2937 Glendower Ave., Los Angeles, Calif.

Filed Mar. 7, 1960, Ser. No. 13,408

1 Claim. (Cl. 47—60)

The present invention relates to a new and distinct variety of chrysanthemum plant obtained by first producing an unnamed and unpatented clear yellow double spoon chrysanthemum by the self-pollination of the unpatented shaggy semi-double spoon chrysanthemum variety "Yellow Exhibition," and then crossing the unnamed and unpatented clear yellow double spoon with an unnamed and unpatented bronze daisy chrysanthemum to produce the present new and distinct variety of chrysanthemum plant.

The object of the foregoing was to obtain a new and different chrysanthemum variety which would have a new and unusual color, and a sweet fragrance which would last for a relatively long period of time.

The resulting variety is an entirely new and distinct chrysanthemum plant having characteristics which easily distinguish it from its parents and from any other variety of chrysanthemum plant known to me.

One of the outstanding characteristics of my new variety which distinguishes it as a new and distinct chrysanthemum plant is its pronounced sweet, musk-like fragrance, similar to Chinese magnolia. This fragrance lasts for the life of the flower, 4 weeks.

My new variety is a stiffer plant than either of its parents and grows taller than the "Yellow Exhibition" parent but shorter than the bronze daisy parent. My new variety has more flowers than the "Yellow Exhibition" parent, but a looser cluster than the bronze daisy parent.

The flowers of my new variety have a distinct coloration which is another outstanding characteristic of this new chrysanthemum. The distal or outer one-third of the petals of the mature flower are Orange-Buff in color, shading into Capucine Yellow for the remaining two-thirds of the inner or proximal part of the petals. The center of the flower is also Capucine Yellow in color. The color of the mature flower of my new variety remains constant and is not subject to the slight fading which occurs to the "Yellow Exhibition" parent.

The flowers of my new variety are approximately 2½ to 3 inches in diameter, without disbudding. If a cluster containing normally 16 to 17 blooms is disbudded to 6 or 7 blooms, the flower size increases to 3 or 4 inches in diameter.

At the budding stage of my new variety, the bud has petals with a color of Mikado Orange streaked with Pompeian Red. The outer ¼ or distil tip of the bud has a color of Brazil Red.

The blooming period of my new variety begins in the first part of October, earlier than the bronze daisy parent, and lasts until November 20 or in some cases to November 30. Individual flowers on a spray of my new variety open about the same time. Cultivation of my new variety was in the frost free climate of Los Angeles, California.

The plant of my new variety is an upright with a height ranging from 26 to 30 inches. It is naturally upright but cascades easily. It can be pruned and maintained much shorter.

The bud of the new variety elongates as it grows. The center of the flower shows as the petals open.

I have performed asexual reproduction of my new variety of chrysanthemum plant by cuttings through several succeeding generations at Los Angeles, California. All of the foregoing characteristics and distinguishing features of my new variety were transmitted true to form through each of the succeeding generations.

The accompanying color photograph shows typical specimens of the vegetation, flowers, and buds of my new variety.

A detailed description of my new variety follows, with all references to color being in accordance with Ridgway's Color Standards and Nomenclature.

Parentage: An unnamed and unpatented clear yellow double spoon crossed with an unnamed and unpatented bronze daisy.

Classification: Single spoon.

Growth: An upright ranging from 26 to 30 inches in height; naturally upright but cascades easily. Can be pruned and maintained much shorter.

Cold resistance: No testing was made of cold resistance since the plant was cultivated in a frost free climate.

Blooming period: From October 10 to November 20 and for some plants on to November 30, under the climatic conditions prevailing in Los Angeles, California.

*Flower*

Bud: The bud elongates as it grows. As the petals open, the center shows. Color: Outside of bud—Mikado Orange, Plate 3, streaked with Pompeian Red, Plate 13; distal tip or outer ¼ of bud—Brazil Red, Plate 1.

Bloom:

*Size.*—2½ to 3 inches in diameter; disbudding increases the size to 3 to 4 inches in diameter.

*Stem.*—Medium stiff; does not require support if kept low. Cascades if allowed to grow tall.

*Form.*—Single spoon.

*Petalage.*—3 to 4 rows of petals.

*Petals.*—Long, narrow, supple, velvety textured petals ending with a point.

*Fragrance.*—A pronounced sweet, musk-like fragrance similar to Chinese magnolia.

*Color.*—Center of flower—Capucine Yellow, Plate 3. Distal or outer ⅓ of petals—Orange-Buff, Plate 3. Proximal or inner ⅔ of petals—Capucine Yellow, Plate 3.

*Plant*

Form: Upright, rounded. Cascades readily.

Growth: Medium height. Can be pruned to be maintained lower.

Foliage: Normal.

*Size.*—Leaf length is 2½ to 3½ inches.

*Quantity.*—Generous.

*Texture.*—Fine grained.

*Color.*—Upper side—Cedar Green, Plate 6. Reverse side—Andover Green, Plate 47.

I claim:

A new and distinct variety of chrysanthemum plant, substantially as shown and described herein, characterized particularly as to novelty by the pronounced sweet musk-like fragrance of its flowers, the relatively long duration of the fragrance, and the distinctive coloration of the petals of the open flower, having in the proximal portion of the petals a Capucine Yellow color tonality shading into Orange-Buff as the distal portion of the petals is approached.

No references cited.